US007864062B2

(12) United States Patent
Cook et al.

(10) Patent No.: US 7,864,062 B2
(45) Date of Patent: Jan. 4, 2011

(54) APPARATUS AND METHOD FOR DETECTING A CHANGE IN A SPECIFIC GRAVITY OF A FLUID

(75) Inventors: Stephen W. Cook, Chardon, OH (US); Michael A. Hemann, Newbury, OH (US); Steven M. Hoopes, Warren, OH (US); Jerome P. Kovach, Auburn, OH (US)

(73) Assignee: Kinetico Incorporated, Newbury, OH (US)

( * ) Notice: Subject to any disclaimer, the term of this patent is extended or adjusted under 35 U.S.C. 154(b) by 280 days.

(21) Appl. No.: 11/666,947

(22) PCT Filed: Nov. 4, 2005

(86) PCT No.: PCT/US2005/040179

§ 371 (c)(1),
(2), (4) Date: Apr. 25, 2008

(87) PCT Pub. No.: WO2006/052832

PCT Pub. Date: May 18, 2006

(65) Prior Publication Data

US 2009/0038396 A1    Feb. 12, 2009

(51) Int. Cl.
*G08B 21/00* (2006.01)

(52) U.S. Cl. .................. 340/603; 340/500; 340/540; 340/623; 340/627; 73/32 R; 73/440; 73/29.05; 73/30.01; 73/30.04; 137/91; 137/98; 137/125; 137/128; 210/85; 210/86; 210/87; 210/97

(58) Field of Classification Search .............. 340/603, 340/540, 623, 627; 73/440, 32 R, 30.01, 73/30.04, 31.05, 434, 451, 29.05, 437, 447, 73/448, 452; 137/71–76, 551–555, 131, 137/161, 165, 264, 242, 434; 210/97, 171, 210/85–89
See application file for complete search history.

(56) References Cited

U.S. PATENT DOCUMENTS

| 1,424,403 | A |   | 8/1922  | Hartman et al.        |
| 2,631,183 | A |   | 3/1953  | Babis                 |
| 5,273,070 | A |   | 12/1993 | Chili et al.          |
| 5,623,251 | A |   | 4/1997  | Clark                 |
| 6,818,126 | B2 | * | 11/2004 | Larson ......... 210/171 |
| 7,387,722 | B1 | * | 6/2008  | Varner et al. ...... 210/97 |

OTHER PUBLICATIONS

International Search Report PCT/US05/40179.
US 2002/0017495 A1 (Ilzuka et al); published Feb. 14, 2002.
US 2003/0052060 A1 (Teel); published Mar. 20, 2003.

* cited by examiner

*Primary Examiner*—George A Bugg
*Assistant Examiner*—Sisay Yacob
(74) *Attorney, Agent, or Firm*—Tarolli, Sundheim, Covell & Tummino LLP

(57) ABSTRACT

Provided is an apparatus for detecting a change in a specific gravity of a fluid surrounding the apparatus wherein the fluid moves upwardly and downwardly with respect to the apparatus. The apparatus includes a housing having a top and a plurality of openings for allowing the fluid to enter the housing. A first floatation device is provided having a first specific gravity and being located within the housing. The first floatation device includes a magnet. A second floatation device is provided having a second specific gravity and located within the housing adjacent said first floatation device. The said second floatation device includes a magnet aligned to have the same polarity as the magnet of the first floatation device. A switch fixedly attached to said top, the switch having an open state and a closed state where when one of said magnets is in proximity to the switch, the switch is in a closed state and wherein when both of said magnets are in proximity to said switch, the switch is in an open state. A signaling device is coupled to the switch wherein said signaling device is activated when the switch is in the closed state.

42 Claims, 6 Drawing Sheets

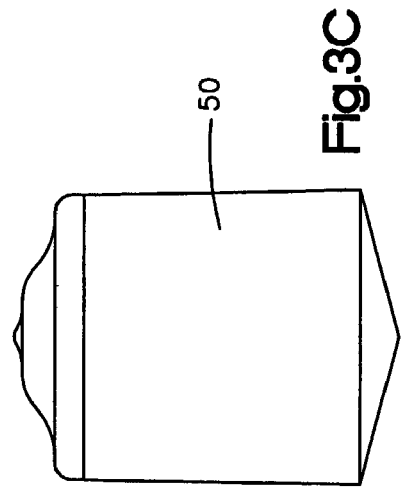
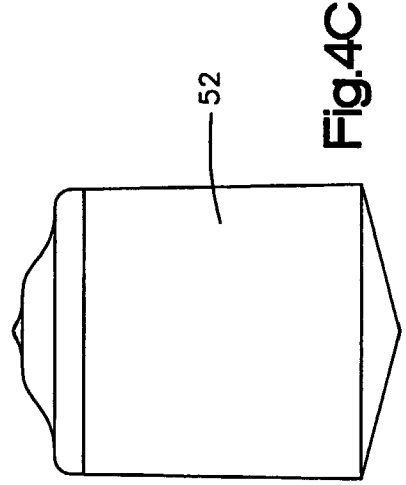
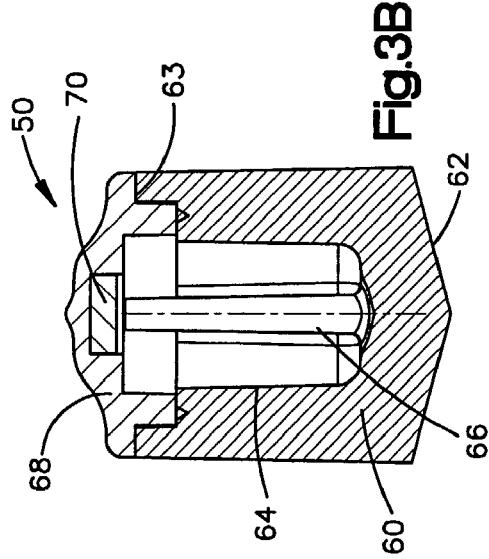
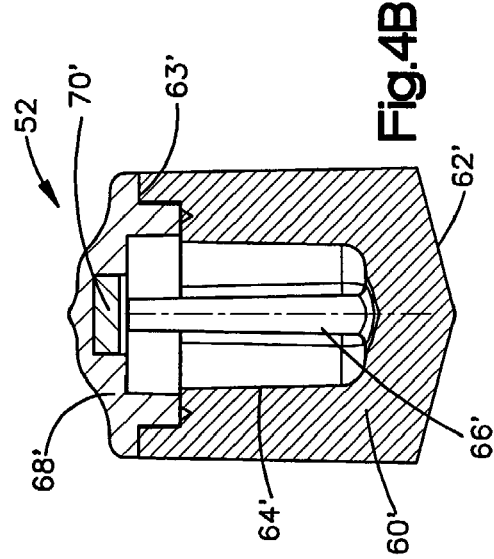
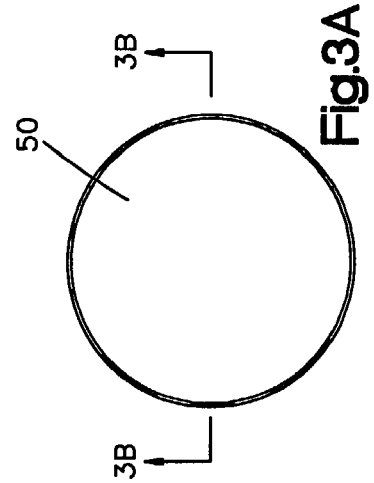
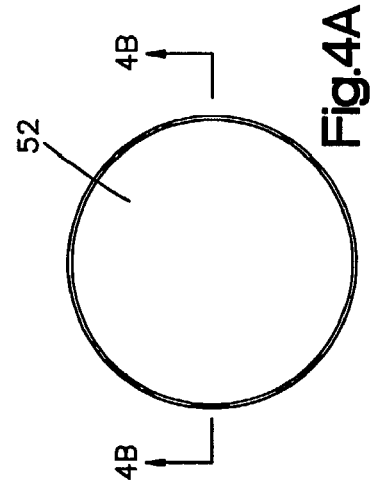

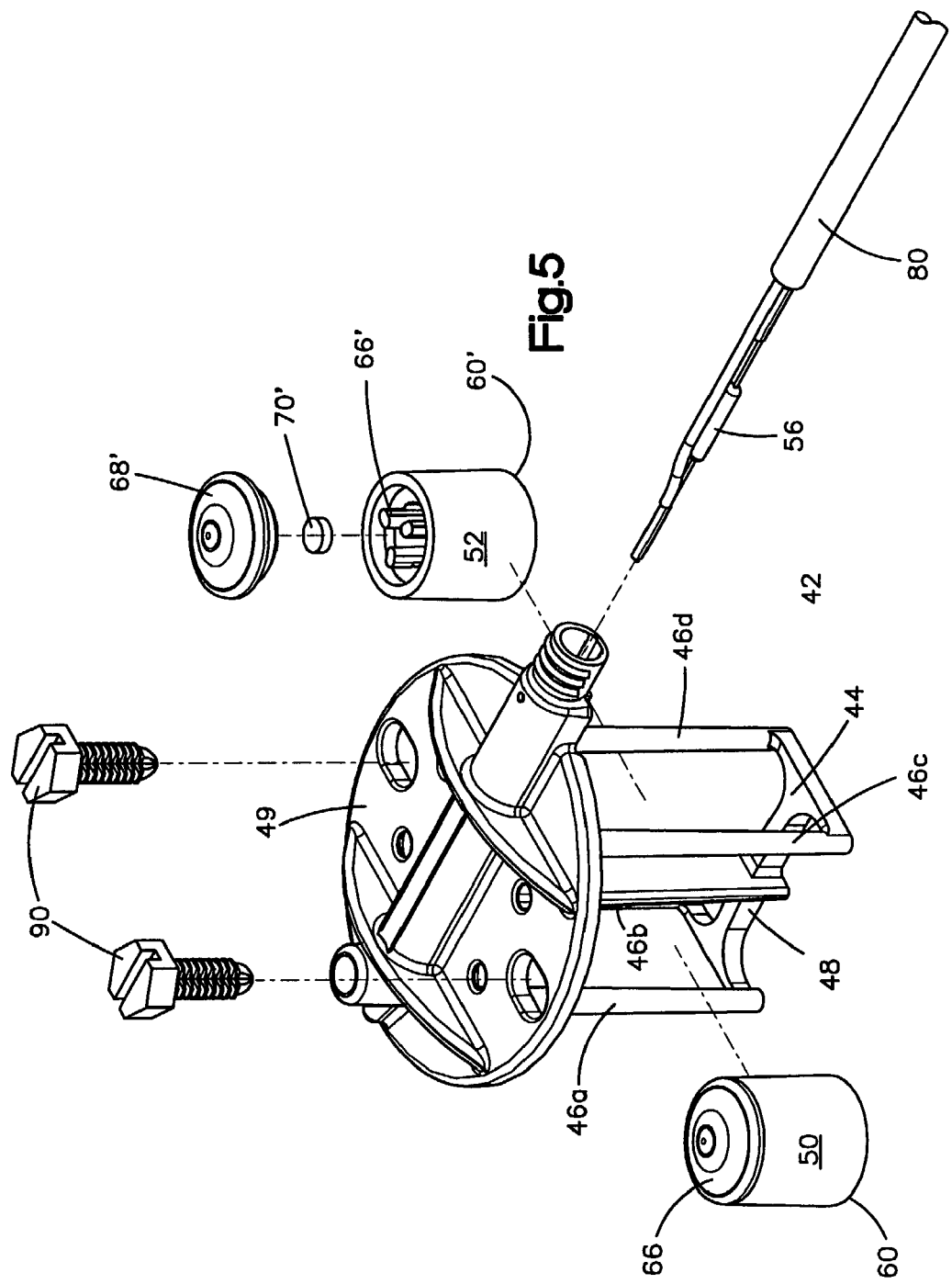

APPARATUS AND METHOD FOR DETECTING A CHANGE IN A SPECIFIC GRAVITY OF A FLUID

FIELD OF THE INVENTION

The present invention relates to an apparatus for use in a fluid treatment system, and, more specifically, to an apparatus for detecting a change in the specific gravity of a brine solution within a brine tank as part of a fluid treatment system.

BACKGROUND

A known water softening apparatus includes a brine tank. The brine tank includes salt upon which water is added to produce a brine (salt/water solution) which in turn is used to regenerate an exhausted treatment tank in a fluid treatment system. After the exhausted tank is regenerated, the brine solution is then purged from the regeneration tank, not to be used again. To produce more brine, water is added to the brine tank having the salt. The water dissolves a portion of the salt to create more brine.

After each regeneration cycle, the amount of salt in the brine tank is reduced. Eventually, the salt in the brine tank will be depleted and the brine solution formed will not be saturated with salt. This unsaturated brine solution will not sufficiently regenerate an exhausted treatment tank. As a result, salt must be added to the brine tank so that proper regeneration of a treatment tank may take place.

Most modern systems do not include a low salt level sensor. The operator must remember to periodically check the level of salt in the brine tank and add salt as needed. These systems are susceptible to operator forgetfulness and error and thus are not entirely satisfactory. As the salt is necessary for the proper functioning of the system and adding salt is the only regular maintenance most modern systems need.

Previous attempts to incorporate a low salt level sensor were not satisfactory. A weight was used in an attempt to determine the level of solid salt in the brine tank. The weight was supposed to sit on top of the solid salt at the bottom of the tank. One of the problems with sensors of this type is that, when operators would add salt to the brine tank, salt would be poured over the weight and it would be buried and be unable to rise and sense the correct salt level. As a result, the sensing unit would falsely indicate that salt was needed. In addition, the salt level did not drop in a uniform manner and the salt would become unevenly distributed and the sensing device would falsely indicate that salt was needed when an adequate supply was present.

In view of the foregoing, a salt level sensor is needed which can accurately relay when salt is actually needed without producing a frequent false alarm that salt levels are low or depleted in the brine tank.

SUMMARY OF THE DISCLOSURE

Disclosed is an apparatus for detecting change in the specific gravity of a fluid and signaling that a change has occurred in the specific gravity. In a preferred embodiment, the apparatus is used in conjunction with a water treatment system to detect a change in the specific gravity of the brine solution to signal when there is low or no salt in the brine tank.

The apparatus is positioned in a brine tank and in a surrounding relationship with the fluid. The apparatus is adapted to detect a change in a specific gravity of a fluid surrounding the apparatus when the fluid moves upwardly and downwardly in the tank with respect to the apparatus. In the preferred embodiment, the apparatus includes a housing having a plurality of openings for allowing the fluid to enter the housing. The housing also includes a top. A first floatation device having a first specific gravity is positioned in the housing. The first floatation device can move freely within the housing in response to the rise and fall of fluid about the apparatus. A second floatation device having a second specific gravity is also positioned in the housing adjacent to the first floatation device. The second floatation device can move freely within the housing in response to the rise and fall of fluid about the apparatus. A sensing element is fixedly attached to the top. The sensing element is adapted to recognize the proximity of the floatation devices to the sensing element. A signaling device is coupled to the sensing element wherein the signaling device is activated by the state of the sensing element.

In a preferred embodiment, the apparatus includes a cage that houses the two floatation devices where each floatation device includes a magnet positioned at its upper end being oriented to have the same polarity or orientation. The housing includes a cap that houses a magnetic reed switch.

In a preferred embodiment, the reed switch includes a pair of contacts, each contact being in communication with a post that extends out of the reed switch encapsulation. Further, these posts are connected to a wire that is in communication with a signaling device. A signaling device can be any device known in the art in view of this disclosure. Examples of such a signaling device include a visual signaling device such as an light emitting diode (LED) or an audible signal such as an alarm.

The floatation devices are of the same construction but are made from different materials thereby having different specific gravities. The floatation devices are, preferably, injection molded. In a preferred embodiment, the floatation devices include a protrusion at either end which aids in minimizing water tension during operation of the apparatus.

In a preferred embodiment, normal operation of a brine drum used in fluid treatment, i.e., water softening systems, brine solution is drawn out of the brine tank by the valve control through conduit and used for regeneration of the fluid treatment tanks. Once the exhausted tank is regenerated, water is pumped back into the brine tank by the valve control through conduit in order to produce more brine for future tank regeneration. As water is added to the brine tank, the salt in the tank dissolves in the water thus producing saturated brine. Through continuous cycles, the salt is depleted and more salt must be added to the brine tank to ensure that the brine is of sufficient concentration to regenerate an exhausted tank. When the salt level is full or adequate, the brine takes on a certain specific gravity. As the salt is depleted, the specific gravity of the brine will change. In a preferred embodiment, one of the floatation devices has a lower specific gravity than the other floatation device.

In the preferred operation, when the brine is in a saturated state or a state having sufficient dissolved salt to regenerate a treatment tank, both floatation devices rise to the top of the apparatus housing as the brine moves upwardly and downwardly during a regeneration cycle. This upwardly and downwardly movement is a direct result of the specific gravities of the flotation devices with respect to the specific gravity of the fluid. It must also be noted that the two-floatation device may be employed to detect a change is specific gravity of a fluid that does not rise and fall in a tank. In this case, the floatation devices will float or sink when there is a change in the specific gravity of the fluid. When used in a treatment system including a brine tank where the level of the water changes during use of the brine, the floatation devices respond to the rise and fall of the water in relation to the specific gravity of the fluid. In this type of system, when the fluid reaches a specific gravity that is between the specific gravities of the floatation devices, it can trigger an alarm signally a change in the specific gravity. Since the alarm can only be triggered by a change is specific gravity of the fluid, a false alarm due to the rise and fall of the fluid in a tank is prevented.

In the preferred operation, the magnets in each floatation device provide an equal influence on the magnetic reed switch thus keeping the contacts in an open state. When the salt in the tank becomes depleted, the specific gravity of the brine becomes less creating a less saturated condition. In this condition, the floatation device having the higher specific gravity will remain at the bottom of the apparatus while the floatation device having the specific gravity closer to water will rise to the top of the apparatus. The magnet in the floatation device that has risen to the top of the apparatus interacts with the contacts in the reed switch causing the contacts to contact each other. The switch closes completing a circuit which activates the signaling device.

In a preferred embodiment, when the two floatation devices are at the top of the apparatus, each magnet interacts with the contacts in the switch causing the contacts to repel one another. In this way, the hysteresis tendency of the contacts to remain closed is reduced. Thus, on the successive brine fill upon addition of salt, the contacts will be forced apart due to the interaction of both magnets on the contacts.

The present invention is also directed to a method for detecting a change in a specific gravity of a fluid. The preferred method includes first providing a supply tank including a fluid that is used in the regeneration of a treatment tank in a fluid treatment system wherein the fluid moves upwardly and downwardly within the tank during a regeneration cycle. Next an apparatus is provided and is fixedly disposed in the supply tank. The apparatus is in a surrounding relationship with said fluid and is adapted to detect a change in the specific gravity of the fluid as the fluid moves upwardly and downwardly within the tank. A signaling device is further provided which is activated by said apparatus when the apparatus detects a change in the specific gravity of the fluid.

Additional features of the invention will become apparent and a fuller understanding obtained by reading the following detailed description made in conjunction with the accompanying drawings.

BRIEF DESCRIPTION OF THE DRAWINGS

FIG. 3 is a cross-sectional view of a floatation device for use in the signaling device of FIG. 2;

FIG. 4 is a cross-sectional view of a floatation device for use in the signaling device of FIG. 2;

FIG. 5 is an exploded perspective view of the signaling device of FIG. 2;

DETAILED DESCRIPTION

Figure 1:
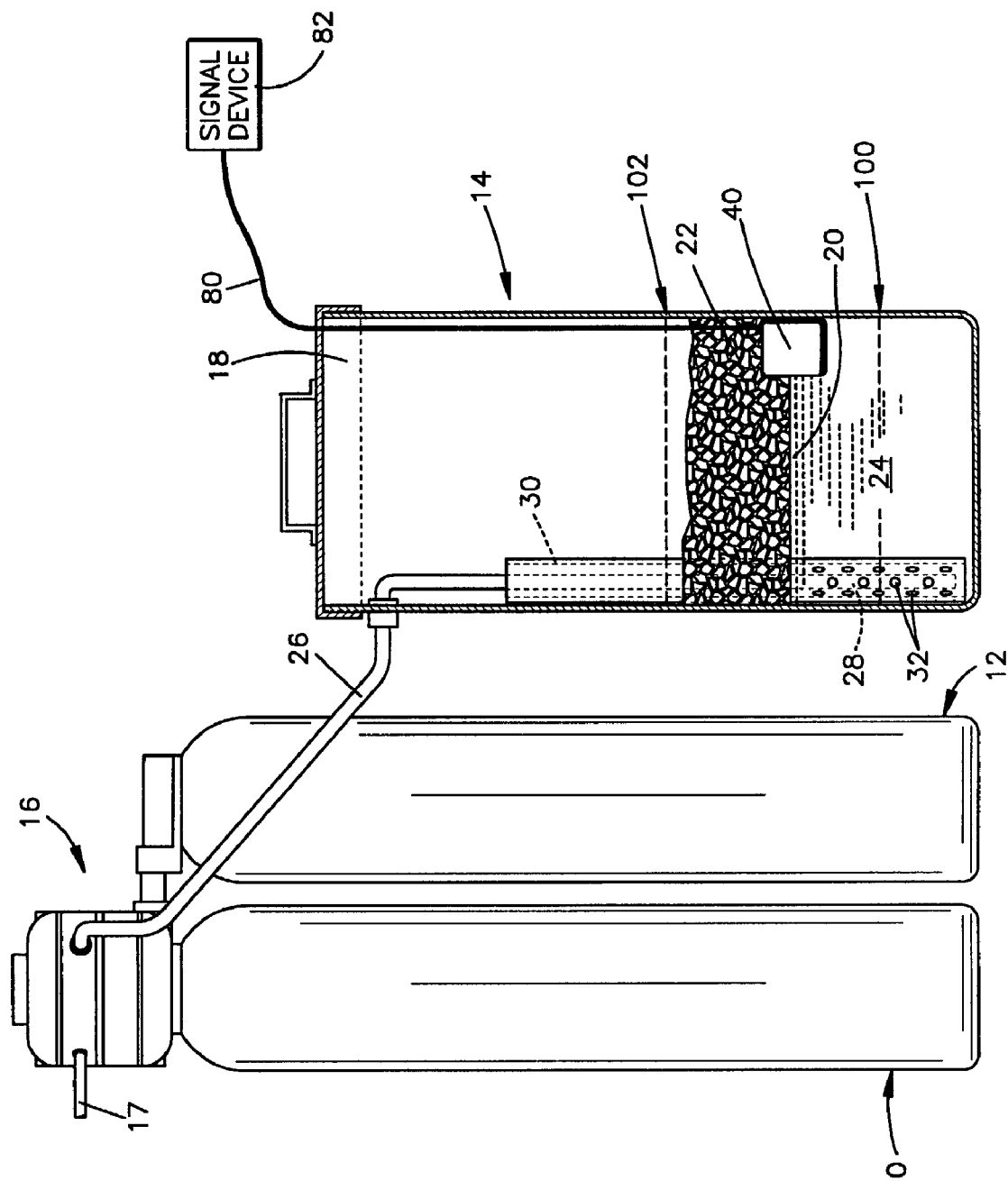
FIG. 1 is a perspective view of a water treatment system employing a signaling device according to the present invention.

FIG. 1 illustrates the overall construction of a water softener system that incorporates the present invention. Although a water treatment system is described, the present invention can be employed in any system where fluid treatment is desired. The system shown includes a pair of fluid treatment tanks 10, 12, an upstanding brine tank 14 and a valve assembly 16 fastened to the tanks 10, 12. The valve 16 controls the usage and regeneration of the tanks 10, 12 and is operative to connect one of the tanks 10, 12 to a water supply or other supply where fluid treatment is required and further controls the regeneration of an exhausted tank. A drain conduit 17 connected to the valve 16 discharges brine solution and "backwash" fluid during a regeneration cycle.

The brine tank 14 is of known configuration and comprises a cylindrical, upstanding container capped by a removable cover 18. A salt grid 20 is disposed horizontally across the container a predetermined distance above the bottom. A granular salt supply, indicated generally by the reference character 22, is supported by the horizontal grid 20. A brine solution reservoir 24 is then defined below the grid 20. The reservoir 24 communicates with the valve assembly 16 through a conduit 26, the fluid communication being controlled by a brine valve 28 (shown schematically). The brine valve is disposed within a brine well 30 that comprises a downwardly extending tube having apertures 32 at its lower end through which the brine solution is admitted. The brine valve 28 serves a dual function in that it controls both the outflow of brine solution from the reservoir 24 to the valve assembly 16 and the inflow of water to replenish the brine solution used during regeneration.

Figure 2:
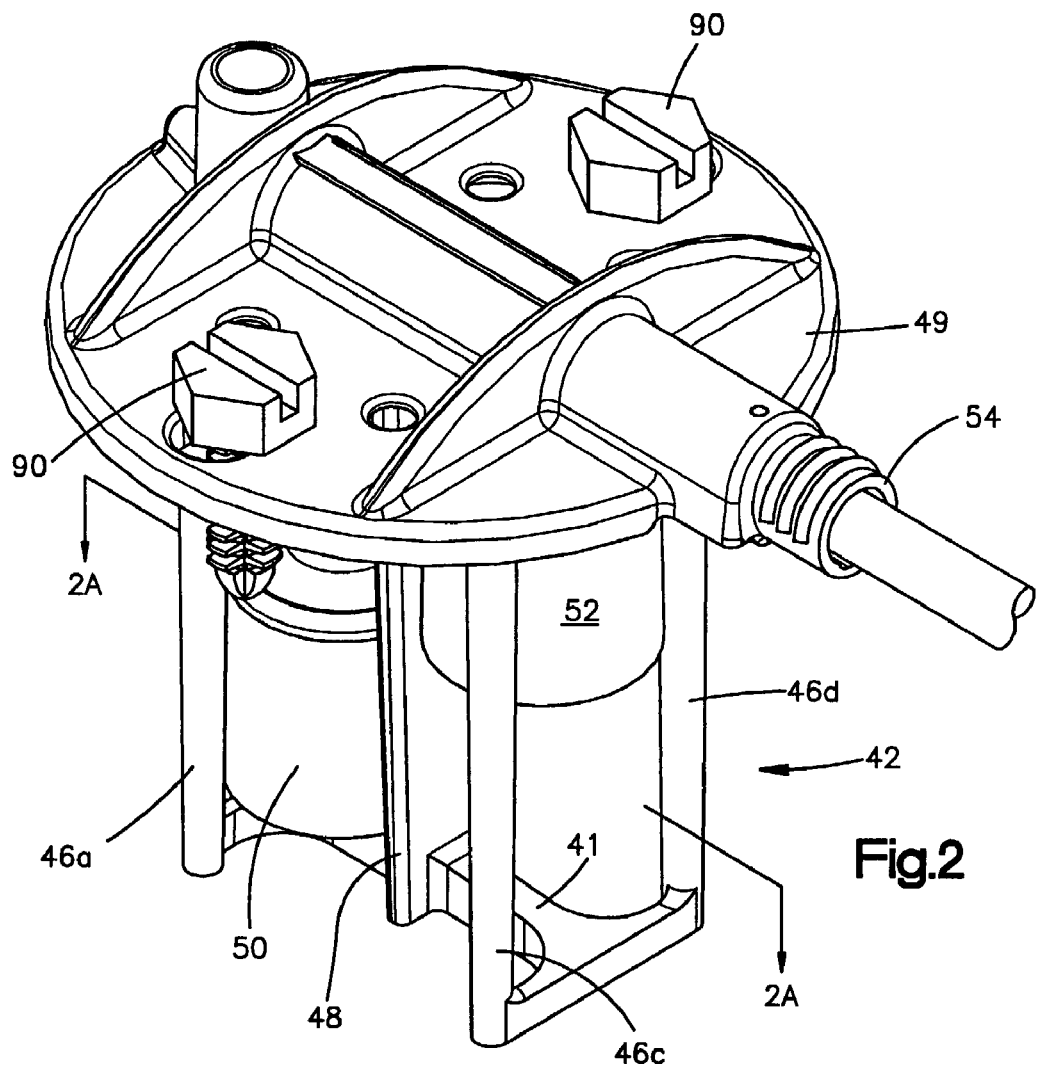
FIG. 2 is a perspective view of a signaling device according to the present invention.
Figure 2A:
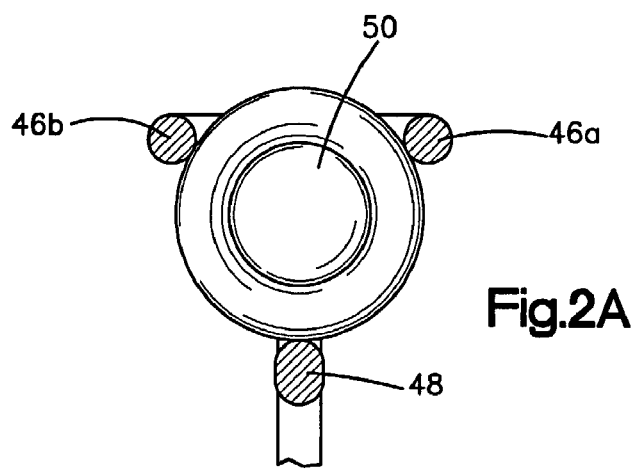
FIG. 2a is a top plan view of the signaling device of FIG. 2 shown from line 2a-2a of FIG. 2.
Figure 6:
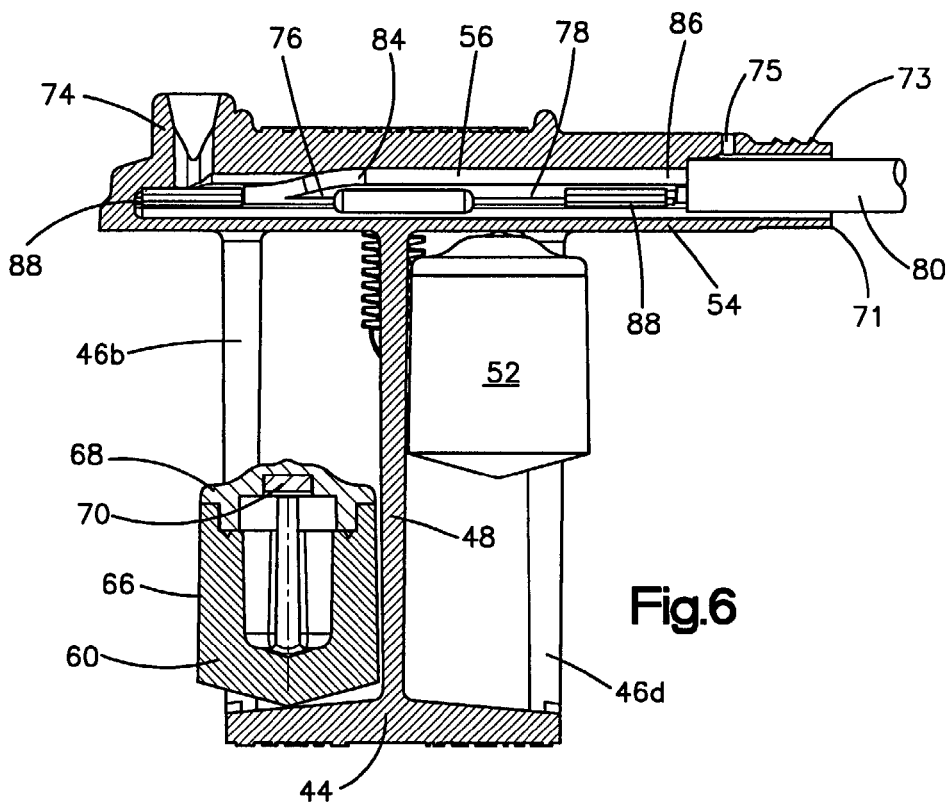
FIG. 6 is a cross-sectional view of the signaling device of FIG. 2.
Figure 7:
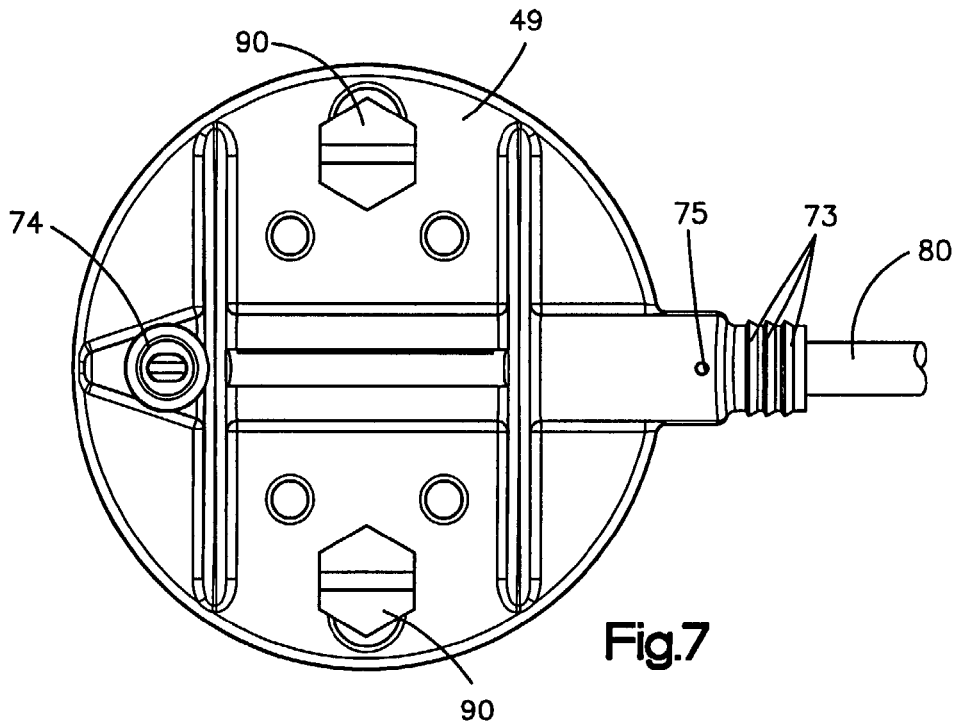
FIG. 7 is a top view of the signaling device of FIG. 2.
Figure 8:
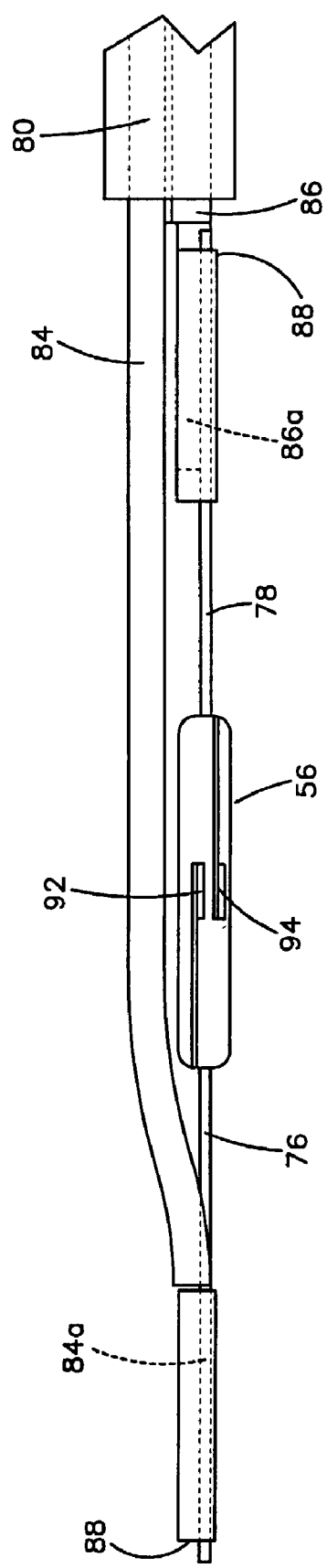
FIG. 8 is a front elevational view of a reed switch for use in the signaling device of FIG. 2.

In the illustrated embodiment, a sensing device 40 is affixed to the salt grid 20. The sensing device 40 is configured to sense when the brine solution in the brine tank 14 is approaching a specific gravity of that of water, indicating that the brine tank 14 is low in salt. The sensing device is typically held in place through mechanical means such as being bolted to the grid, however, other attachments means are also contemplated such as, adhesives or other bonding techniques. Turning to FIGS. 2-8, the brine sensing device 40 is shown in more detail. The sensing device includes a cage structure 42 having an I-shaped base 44, four outer retaining elements 46 a-d and a central retaining element 48 each of which extend generally perpendicularly away from the base 44 to an opposing cage top 49. The retaining elements 46a and 46b along with the central retaining element 48 define one portion of the cage structure 42 that houses a first floatation device 50. Likewise, retaining elements 46c and 46d along with the central retaining element 48 define a second portion to the cage structure 42 that houses a second flotation device 52. FIG. 2a illustrates the preferred configuration for housing the floatation device 50 within the cage structure 42. The retaining element 46a is spaced a distance from the retaining element 46b by a distance less than the diameter of the floatation device 50. Furthermore, the retaining elements 46a and 46b are spaced a distance from the central retaining element 48 by a distance less than the diameter of the floatation device 50. In this configuration, the flotation device 50 is confined by the retaining elements 46a and 46b and the central retaining element 48 at three points and is permitted to freely flow for the length of the retaining elements 46a and 46b and central retaining element 48. This limits friction so that the floatation device 50 can easily move with respect to the level of solution within the brine tank 14 where the specific gravity of the fluid is higher than that of the floatation device 50. FIG. 2a shows the configuration with respect to floatation device 50, however, this same configuration is employed with respect to floatation device 52. In this regard, floatation device 52 is confined by retaining elements 46c and 46d along with the central retaining element 48. This configuration secures the first floatation device 50 and the second floatation device 52 such that they are positioned directly over the top 49 being a predetermined horizontal distance from each other. This configuration also provides a known travel path of the floatation devices 50 and 52 within the cage 42 in response to the rise and fall of water/brine within the tank 14.

FIGS. 3 and 4 illustrate the detail of the first flotation devices 50 and second floatation device 52. The first floatation device 50 and the second floatation device 52 are of identical construction, however, they differ with respect to their overall specific gravities. Turning to FIG. 3, the first floatation devices 50 includes a substantially cylindrical base 60 having somewhat cone-shaped bottom surface 62 and an opposing open top end 63. The cylindrical base 60 includes a slot or cavity 64 that extends from the open end 63 into the cylindrical base 60 providing a hollow center to the floatation device 50. A series of prongs 66 (shown best in FIG. 3 with respect to the second floatation device 52, prongs labeled as 66') extend from the bottom of the slot 64 upward toward the open end 63. A cap 68 is positioned over the open end 63 of the cylindrical base 60 is welded in place via ultrasonic welding. Other methods of adhering the cap to the base are likewise contemplated such as the use of an adhesive or through a series of mechanical fixtures. Regardless of the method use to secure the cap 68 to the cylindrical base 60, a fluid-tight seal must be attained so that no water or brine is permitted to enter the flotation device 50. The cap 68 includes a slight arch of the top. This arch along with the cone shape on the bottom of the base 60 acts to minimize water tension on the top and bottom of the floatation device, respectfully. Further, a magnet 70 is seated in the cap 68 prior to securing the cap 63 to the base 60. The magnet 70 is centrally positioned in the cap 68 and is located and held in the cap 63 by the prongs 66. The magnet in the first floatation device 50 is positioned to have the same polarity as the magnet 70' of the second floatation device 52 (i.e., the north and south end of each magnet point in the same direction).

The first floatation device 50 has a specific gravity of about that of a saturated solution. In the illustrated embodiment, the specific gravity is greater than that of water or greater than 1.0 $g/cm^3$. To obtain such a specific gravity, the cap 68 and base 60 of the first floatation device 50 are constructed from a plastic material that has a specific gravity greater than that of water. Such plastic material may be filled, if necessary, with a filler material such as glass or other materials as known to those of ordinary skill in the art. One such plastic material that provides a useable specific gravity greater than water for the first floatation device 50 is a polyphenylene ether/PPO, polystyrene plastic commonly referred to as Noryl GFN3 and is commercially available from General Electric Company. Typically, this construction produces a first floatation device 50 (including the base 60, cap 68 and encapsulated magnet 70) having a specific gravity greater then 1.0 $g/cm^3$. Yet, depending on the amount of fill in the plastic material, a specific gravity in the range from greater than 1.0 $g/cm^3$ to about 1.21 $g/cm^3$ can be obtained. In the case of a water softening system employing a brine tank, a first floatation device 50 having a specific gravity of about 1.21 $g/cm^3$ is desired.

As discussed, the first flotation device 50 has the same overall construction as the second floatation device 52. However, the floatation devices are each of a different specific gravity. Referring to FIG. 4, the second floatation device 52 illustrated. The second floatation device 52 is constructed from a plastic material and is formed via injection molding of the base 60' and cap 68'. The base 60' and cap 68' are then welded together by an ultra-sonic weld. The cap 68' and base 60' of the second floatation device 52 is constructed of a plastic material which should have a specific gravity close to that of water (1.0 $g/cm^3$). One such material is an acrylonitrile-butadiene-styrene copolymer and is commonly known. Use of this material produces a water floatation device having an overall specific gravity in the range from less than 1.0 $g/cm^3$ to about less than 1.21 $g/cm^3$. However, the specific gravity to be employed is dependent on the fluid the floatation device is be used in and the specific gravity must be less than that of a first floatation device 50. In the case of a water treatment system employing a brine tank, a second floatation device 52 having a specific gravity of about 0.98 $g/cm^3$ is desired.

In some cases, when the first floatation device 50 and second floatation device 52 are constructed the desired specific gravity is not obtained. When this happens, weights such as small brass balls may be added to the floatation device 50, 52 to modify the specific gravity. The brass balls (not shown) are of known weight and are placed in the slot or cavity 64 or 64'. Once the correct specific gravity is obtained with the addition of the brass balls the cap 68 or 68' can be welded to the base 60 or 60' to prevent any further changes to the floatation devices specific gravity by a fluid leaking into the first floatation device 50 or second floatation device 52.

The cage top 49 is a generally circular in nature and adapted to support or retaining element 46 a-d of the cage 42. The cage top 49 includes a generally horizontal passage 54 that extends across the cage top 49 from a passage inlet 71 to a passage outlet 74. The passage 54 further includes an overflow bore 75. This passage 54 houses a magnetic reed switch 56.

The reed switch 56 is a standard reed switch and is commercially available. The reed switch 56 (referring to FIG. 8) includes two wire posts 76, 78 that extend out of the glass encapsulated reed contact or reed switch 56. During operation, the wire posts 76, 78 act as an antenna to interact with the magnetic flux of the magnet 70 or 70' in the first floatation device 50 and the second floatation device 52. A jacketed cable 80 is affixed to the wire post 76, 78 to carry an electronic signal from the reed switch 56 to an alarm or signaling device 82. The signaling device 82 (FIG. 1) can be a variety of different signaling devices such an LED, an audible alarm and/or an input to an electronic device. The jacketed cable 80 has two insulated wires 84 and 86 which contact the wire posts 76 and 78, respectively. Typical wire as used for the wires 84 and 86 have an insulating coating which is removed to expose the metal wire for making an electrical connection. In this case, a portion of the insulated wire 84 is stripped away exposing the metal core 84a. The metal post 76 and the metal core 84a are both inserted into a wire ferrule 88 and the ferrule is crimped to make a secure connection between the metal core 84a and the metal post 76. Likewise, the second insulated wire 86 is stripped to expose the metal core 86a. The metal post 78 and metal core 86a are inserted into a ferrule 88 and the ferrule 88 is crimped to make a secure connection between the metal core 86a and the metal post 78. Although a crimped ferrule is use to connect the metal posts 76 and 78 to the wire cores 84a, 86a, other techniques may be employed to provide an electrical connection. One other such technique is soldering. Encapsulated in the reed switch 56 are a first contact 92 and an opposing second contact 94. The first contact 92 is coupled to the metal post 76 and the second contact 94 is coupled to metal post 78. In their normal position, the first contact 92 is separated from the second contact 94, thus, producing an open switch. As explained below, the contacts 92 and 94 can contact each other to close the circuit thereby activating the signal device 82.

Once the reed switch 56 is connected to the jacketed cable 80, it is inserted into the passage 54 through the passage inlet 71 far enough so that at least a portion of the jacketed cable 80 enters the passage 54. To secure and protect the reed switch 56 within the passage 54, a potting compound is injected into the passage outlet 74. The potting compound fills the passage 54 housing the reed switch 56 and associated components thereby encapsulating the reed switch 56. The potting compound is continuously injected into the passage outlet 74 until there is an overflow of potting compound exiting the overflow bore 75. At this point, injection of the potting complete is complete encapsulating the reed switch 56 in the passage 54 and protecting the reed switch 56 from the water/brine solution and physically protecting the reed switch 56 from damage. Potting compounds suitable for use in potting the passage 54 are commonly known and within one of ordinary skill in the art to develop. The passage inlet 71 includes ribs 73 on its outer peripheral upon which wire shrink wrap is utilized to make a seal between the cap 49 and jacketed cable 80 as well as provide mechanical strain relief on the cable connection to the passage 54.

The brine sensing device 40 is positioned in the brine tank in the salt grid 20. The cage top 49 includes a pair of spin/push clips 90 that secure into a receptacle (not shown) on the salt grid 20 such that the cage top rest in contact with the salt grid 20 and the cage portion extends below the salt grid 20. In this configuration, the sensing device 40 remains in place as the fluid rises and falls with respect to the sensing device 40. In turn, the floatation devices 50 and 52 are permitted to move with the fluid provided that the specific gravity of the first floatation device 50 and second floatation device 52 is less than the specific gravity of the fluid.

Operation:

During the normal operation of a brine drum used in fluid treatment, i.e., water softening systems, brine solution is drawn out of the brine tank 14 by the valve control 16 through conduit 26 and used for regeneration of the fluid treatment tanks 10, 12. Once the exhausted tank, either 10 or 12, is regenerated, water is pumped back into the brine tank by the valve control 16 through conduit 26 in order to produce more brine for future tank regeneration. This use and replenishing causes the level of brine in the brine tank 14 fluctuate. The brine sensing device 40 is typically positioned on the salt grid 20 where the lower level, indicated by the arrow 100 in FIG. 1, of the brine after the brine is drawn from the tank is at least 0.5" below the salt grid 20 and the upper level, indicated by the arrow 102 in FIG. 1, of the brine after water is added for replenishing brine must be above the salt grid 20 for normal operation of the sensing device 40. This placement of the sensing device ensures that the sensing device 40 is not located in a brine layer which commonly forms at the bottom of a brine tank.

Prior to brine being supplied to a tank 10, 12 for regeneration, the brine level is at the upper level 102 within the brine tank 14. Due to the presence of salt within the tank 14, the solution is saturated. At this point, the saturated solution has a specific gravity that is much greater than that of water and is near or about 1.21 g/cm$^3$. As stated, the first floatation device 50 has a specific gravity of about 1.20 g/cm$^3$ and second floatation device 52 has a specific gravity of about 0.98 g/cm$^3$. Therefore, both of the floatation devices 50 and 52 will be at the top of the cage 42 since each floatation device has a specific gravity less than the of the saturated solution.

In this position, the magnetic flux of the magnet 70 in the first floatation device 50 interacts with the metal post 76 of the reed switch 56. Similarly, the magnetic flux of the magnet 70' in the second floatation device 52 interacts with the metal post 78 of the reed switch 56. The magnetic flux of the magnet 70 in the first floatation device 50 is received by the antenna-acting metal post 76 and is transferred to the first contact 92. Likewise, the magnetic flux of the magnet 70' in the second floatation device 52 is received by the antenna-acting metal post 78 and is transferred to the second contact 94. The magnets 70 and 70' are of the same polarity and this polarity is reflected by the first contact 92 and second contact 94 thus causing the first contact 92 to repel the second contact 94 thus keeping the switch in the open position. Imparting the same magnetic field on the opposite ends of the reed switch 56 ensures that the first contact 92 will repel the second contact 94 reducing the hysteresis tendency of the contacts 92, 94 to remain closed once they have come into contact with each other.

As brine is drawn out of the brine tank 14 during a tank regeneration cycle, the first floatation device 50 and second floatation device 52 begin to drop away from the cap 49 in the cage 42. As the first floatation device 50 and the second floatation device 52 drop away from the cap 49 the magnet 70 in the first floatation device 50 and the magnet 70' in the second floatation device 52 exert less influence on the metal posts 76, 78 thereby reducing the induced magnetic field exerted on the first contact 92 and second contact 94. In some instances, the first floatation device 50 may drop at a faster rate then the second floatation device 52 or vice versa. When this situation occurs, a false signal could result indicating the tank 14 is out of salt. However, there is a maximum distance that the magnet 70 of first floatation device 50 or the magnet 70' of the second floatation device 52 must be within for the contacts 92, 94 to close and over come the mechanical movement of the contacts 92, 94. Because the distance between the magnets 70, 70' and the metal posts 76, 78 is so small, one of the first floatation device 50 or the second floatation device 52 must be very close to the metal posts 76, 78 while the other floatation device must be a considerable minimum distance away before the magnet of the closer floatation device can assert enough magnetic flux on the metal post, which is translated to one of the contacts, to overcome the mechanical movement and minimal influence of the opposing magnet to cause the contact 92, 94 to come into contact, thereby closing the switch. This essentially creates a "deadband" where one of the first floatation device 50 or second floatation device 52 can travel away from the reed switch 56 without causing the contacts 92, 94 to come into contact with each other. Thus, one floatation device can move in the cage 42 prior to the other floatation device without causing a false signal to occur.

When the brine in the tank 14 is drawn to a lower level 100, both floatation devices 50 and 52 move away from the top of the cage 42 at slightly different rates. As long as the floatation device that moves first is within the deadband described above before the other floatation device moves, the contacts 92, 94 will not falsely close. At the brine continues to drop in the tank 14, the floatation devices 50 and 52 drop in the cage 42 as the brine drops to the lower level 100 in the tank 14 without any influence on the reed switch 56.

When the brine is at a lower level 100 within the brine tank 14, the valve 16 permits water to flow into the tank through conduit 26. Some of the saturated brine mixes with the incoming water to create a layer of less concentrated brine solution between the lower brine level and the rising brine/water mixture. This less saturated solution has a specific gravity greater than the of either the first floatation device 50 or the second floatation device 52, thus, the floatation devices 50 and 52 both rise to the top of the cage as the water/brine level increases. As the less saturated solution rises above the salt grid 20, the less saturated solution comes into contact with the salt and begins to further saturate the solution back to a more saturated brine condition. At this time, both floatation devices 50 and 52 stay at the top of the cage 42 and again influence the reed switch 56 equally so that the first contact 92 does not come into contact with the second contact 94.

The described cycle takes place each time one of the tanks 10 or 12 require regeneration. As long as there is salt on the salt grid 20 there will be no significant changes to the specific gravity of the brine solution within the tank 14. However, when a cycle repeats and there is little or no salt on the grid 20, the solution between the lower level 100 and the upper level 102, does not increase in saturation and thus the specific gravity of the solution begins to drop. At this point, the solution may still have a specific gravity greater than that of either the first floatation device 50 or the second floatation device 52 and the floatation devices 50 and 52 are again lowered again on the drawn down cycle of the brine. On the successive water fill, water is injected into a slightly reduced concentration brine solution and the brine concentration is even further reduced. At this point, the specific gravity of the reduced brine is less than that of the of the first floatation device 50 but greater than the of the second floatation device 52. When the refill is occurring, the first floatation device 50 will not rise back to the top of the cage 42. The second floatation device 52, on the other hand, having a specific gravity less than the reduced brine solution will rise to the top of the cage 42. Upon completion of the water refill, the level of the brine in the brine drum 14 is back to the upper level 102 and the first floatation device 50 is at the bottom of the cage 42 and the second floatation device 52 is at the top of the cage 42. Thus the magnet 70' in the second floatation device 52 exerts a magnetic influence on the metal post 78 which is translated to the contact 94. The contact 94 attracts the opposing contact 92 since there is no opposing magnetic influence on the contact 94 from the magnet 70 of the first floatation device 50. As such, the contact 94 attracts the contact 92 closing the switch. The closed switch completes a circuit which sends a current to the signaling device 82 outside of the brine tank 14 signaling that the salt within the tank is low or completely exhausted. This signaling occurs within one to two cycles of a low or depleted salt condition.

Although the invention has been described with a certain degree of particularity, it should be understood that various changes can be made to those skilled in the art without departing from the spirit or scope of the invention as hereinafter claimed

We claim:

1. An apparatus for detecting a change in a specific gravity of a fluid surrounding the apparatus, the apparatus comprising: a housing having a plurality of openings for allowing the fluid to enter the housing, said housing including a top; a first floatation device having a first specific gravity, said first floatation device being located within said housing wherein said first floatation device includes a magnet and wherein said first floatation device can move freely within the housing in response to a change in the specific gravity of the fluid; a second floatation device having a second specific gravity, said second floatation device being located within said housing in proximity with said first floatation device wherein said second floatation device includes a magnet aligned to have the same polarity as the magnet of said first floatation device and wherein said second floatation device can move freely within the housing in response to a change in the specific gravity of the fluid; a switch fixedly attached to said top wherein said switch has an open state and a closed state wherein when one of said magnets is in proximity to the switch, the switch is in a closed state and wherein when both of said magnets are in proximity to said switch, the switch is in an open state; and a signaling device coupled to the switch wherein said signaling device is activated when the switch is in the closed state.

2. The apparatus of claim 1 wherein said housing is a cage-like structure.

3. The apparatus of claim 1 wherein said apparatus is used to detect a change in the specific gravity of brine used for water treatment tank regeneration in a water treatment system.

4. The apparatus of claim 3 wherein one of said first floatation device and said second floatation device has a first specific gravity of about the specific gravity of an unsaturated brine solution and wherein one of said first floatation device and said second floatation device has a second specific gravity of about the specific gravity of a saturated brine solution.

5. The apparatus of claim 4 wherein said first specific gravity is in the range from greater than 1.0 g/cm$^3$ to about 1.21 g/cm$^3$.

6. The apparatus of claim 4 wherein said second specific gravity is in the range from less than 1.0 g/cm$^3$ to about 1.21 g/cm$^3$.

7. The apparatus of claim 4 wherein when the fluid is in a saturated condition, the first floatation device moves at about the same rate within the housing as the second floatation device when the fluid moves upwardly and downwardly with respect to the apparatus and wherein the magnets in each of said first floatation device and said second floatation device equally influence said switch.

8. The apparatus of claim 4 wherein when the fluid is in a less than saturated condition, the one of said first floatation device and said second floatation device having a said second specific gravity remains at the bottom of the housing as fluid moves upwardly with respect to the apparatus and wherein the one of said first floatation device and said second floatation device having said first specific gravity moves upwardly towards the top of the housing as the fluid move upwardly with respect to the apparatus wherein the magnet of the floatation device having said first specific gravity influences the switch causing it to attain a closed state.

9. The apparatus of claim 8 wherein the closed switch activates said signaling device.

10. The apparatus of claim 1 wherein said signaling device is an LED.

11. The apparatus of claim 1 wherein said signaling device is an audible alarm.

12. The apparatus of claim 1 wherein said signaling device is an input for an electronic controller.

13. The apparatus of claim 1 wherein said first floatation device and said second floatation device are positioned in said cage wherein said first floatation device is spaced from said second floatation device at a set predetermined horizontal distance and wherein said first floatation device and said second floatation device are spaced from said switch.

14. The apparatus of claim 1 wherein said switch is a magnetic reed switch.

15. The apparatus of claim 1 wherein said first floatation device and said second floatation device each including a protrusion on the top and bottom, said protrusion on the top and said protrusion on the bottom aiding to minimize water tension.

16. An apparatus for detecting a change in a specific gravity of a fluid surrounding the apparatus, the apparatus comprising: a housing having a plurality of openings for allowing the fluid to enter the housing, said housing including a top; a first floatation device having a first specific gravity, said first floatation device being located within said housing wherein said first floatation device can move freely within the housing in response to a change in the specific gravity of the fluid; a second floatation device having a second specific gravity, said second floatation device being located within said housing in proximity with said first floatation device wherein said second floatation device can move freely within the housing in response to a change in the specific gravity of the fluid; a sensing element fixedly attached to said top wherein said element is adapted to recognize the proximity of the said first floatation device and said second floatation device; and a signaling device coupled to the sensing element wherein said signaling device is activated by the state of the sensing element.

17. The apparatus of claim 16 wherein said sensing element is a magnetic reed switch.

18. The apparatus of claim 16 wherein said apparatus is used in a brine tank as part of a water treatment system.

19. The apparatus of claim 18 wherein one of said first floatation device and said second floatation device has a first specific gravity of about the specific gravity of an unsaturated brine solution and wherein one of said first floatation device and said second floatation device has a second specific gravity of about the specific gravity of a saturated brine solution.

20. The apparatus of claim 19 wherein said first specific gravity is in the range from greater than 1.0 g/cm$^3$ to about 1.21 g/cm$^3$.

21. The apparatus of claim 19 wherein said second specific gravity is in the range from less than 1.0 g/cm$^3$ to no greater than 1.21 g/cm$^3$.

22. The apparatus of claim 17 wherein said reed switch has an open state and a closed state.

23. The apparatus of claim 22 wherein said first floatation device and said second floatation device include a magnet wherein the magnet of the first floatation device and the second floatation device are have the same polarity.

24. The apparatus of claim 23 wherein when the fluid is in a saturated condition, the first floatation device and the second floatation device float within the housing and wherein the magnets in each of said first floatation device and said second floatation device equally influence said switch thereby causing the switch to acquire said open state.

25. The apparatus of claim 22 wherein when the fluid is in a less than saturated condition, the one of said first floatation device and said second floatation device having a said second specific gravity sinks to the bottom of the housing wherein the one of said first floatation device and said second floatation device having a first specific gravity floats within the housing wherein the magnet of the floatation device having said first specific gravity influences the switch causing it to attain a closed state.

26. The apparatus of claim 25 wherein the closed switch activates said signaling device.

27. An apparatus for use in a water treatment system for detecting a change in a specific gravity of a brine solution surrounding the apparatus wherein the brine moves upwardly and downwardly with respect to the apparatus, the apparatus comprising:
a housing having a plurality of openings for allowing the fluid to enter the housing, said housing including a top;
a first floatation device having a first specific gravity, said first floatation device being located within said housing wherein said first floatation device includes a magnet and wherein said first floatation device can move freely within the housing in response to a change in the specific gravity of the fluid;
a second floatation device having a second specific gravity, said second floatation device being located within said housing in proximity with said first floatation device wherein said second floatation device includes a magnet aligned to have the same polarity as the magnet of said first floatation device and wherein said second floatation device can move freely within the housing in response to a change in the specific gravity of the fluid;
a magnetic reed switch fixedly attached to said top wherein said switch has an open state and a closed state wherein when one of said magnets is in proximity to the switch, the switch is in a closed state and wherein when both of said magnets are in proximity to said switch, the switch is in an open state; and
a signaling device coupled to the switch wherein said signaling device is activated when the switch is in the closed state.

28. The apparatus of claim 27 wherein one of said first floatation device and said second floatation device has a first specific gravity of about the specific gravity of an unsaturated brine solution and wherein one of said first floatation device and said second floatation device has a second specific gravity of about the specific gravity of a saturated brine solution.

29. The apparatus of claim 28 wherein said first specific gravity is in the range from greater than 1.0 g/cm$^3$ to about 1.21 g/cm$^3$.

30. The apparatus of claim 28 wherein said second specific gravity is in the range from less than 1.0 g/cm$^3$ to about 1.0 g/cm$^3$.

31. The apparatus of claim 28 wherein when the fluid is in a saturated condition, the first floatation device moves at about the same rate within the housing as the second floatation device when the fluid moves upwardly and downwardly with respect to the apparatus and wherein the magnets in each of said first floatation device and said second floatation device equally influence said switch.

32. The apparatus of claim 28 wherein when the fluid is in a less than saturated condition, the one of said first floatation device and said second floatation device having a said second specific gravity remains at the bottom of the housing as fluid moves upwardly with respect to the apparatus and wherein the one of said first floatation device and said second floatation device having said first specific gravity moves upwardly towards the top of the housing as the fluid move upwardly with respect to the apparatus wherein the magnet of the floatation device having said first specific gravity influences the switch causing it to attain a closed state.

33. The apparatus of claim 32 wherein the closed switch activates said signaling device.

34. A method for detecting a change in a specific gravity of a brine fluid, said method comprising the steps of:
providing a supply tank including a brine fluid that is used in the regeneration of a treatment tank in a fluid treatment system wherein the brine fluid moves upwardly and downwardly within the tank during a regeneration cycle;
providing an apparatus fixedly disposed in said supply tank said apparatus in a surrounding relationship with said brine fluid and is adapted to detect a change in the specific gravity of the brine fluid, said apparatus including a housing and first and second flotation devices having first and second specific gravities, said flotation devices located within said housing; and activating a signaling device when said first and second floatation devices are in predetermined positions within said housing.

35. The method of claim 34 wherein said apparatus comprises:

said housing having a plurality of openings for allowing the brine fluid to enter the housing, said housing including a top;

said first floatation device having said first specific gravity and said first floatation device being located within said housing wherein said first floatation device includes a magnet and wherein said first floatation device can move freely within the housing in response to a change in the specific gravity of the brine fluid;

said second floatation device having said second specific gravity and said second floatation device being located within said housing adjacent said first floatation device wherein said second floatation device includes a magnet aligned to have the same polarity as the magnet of said first floatation device and wherein said second floatation device can move freely within the housing in response to a change in the specific gravity of the brine fluid; and a switch fixedly attached to said top wherein said switch has an open state and a closed state wherein when one of said magnets is in proximity to the switch, the switch is in a closed state and wherein when both of said magnets are in proximity to said switch, the switch is in an open state wherein said signaling device is coupled to the switch, said signaling device being activated when the switch is in the closed state.

36. The method of claim 35 wherein said apparatus is used to detect a change in the specific gravity of brine used for water treatment tank regeneration in a water treatment system.

37. The method of claim 35 wherein one of said first floatation device and said second floatation device has a first specific gravity of about the specific gravity of an unsaturated brine solution and wherein one of said first floatation device and said second floatation device has a second specific gravity of about the specific gravity of a saturated brine solution.

38. The method of claim 35 wherein said first specific gravity is in the range from greater than 1.0 g/cm$^3$ to about 1.21 g/cm$^3$.

39. The method of claim 35 wherein said second specific gravity is in the range from less than 1.0 g/cm$^3$ to about 1.0 g/cm$^3$.

40. The method of claim 37 wherein when the brine fluid is in a saturated condition, the first floatation device moves at about the same rate within the housing as the second floatation device when the brine fluid moves upwardly and downwardly with respect to the apparatus and wherein the magnets in each of said first floatation device and said second floatation device equally influence said switch.

41. The method of claim 37 wherein when the brine fluid is in a less than saturated condition, the one of said first floatation device and said second floatation device having a said second specific gravity remains at the bottom of the housing as fluid moves upwardly with respect to the apparatus and wherein the one of said first floatation device and said second floatation device having said first specific gravity moves upwardly towards the top of the housing as the fluid move upwardly with respect to the apparatus wherein the magnet of the floatation device having said first specific gravity influences the switch causing it to attain a closed state.

42. The method of claim 41 wherein the closed switch activates said signaling device.

\* \* \* \* \*